United States Patent [19]

Racciato

[11] 4,331,440

[45] May 25, 1982

[54] USE OF GUM S-88 IN PRINTING PASTE SYSTEMS

[75] Inventor: Joseph S. Racciato, San Diego, Calif.

[73] Assignee: Merck & Co. Inc., Rahway, N.J.

[21] Appl. No.: 130,797

[22] Filed: Mar. 17, 1980

[51] Int. Cl.$^3$ .................... D06P 1/48; C07G 11/00; C07G 17/001

[52] U.S. Cl. .................................... 8/495; 8/561; 536/123; 536/114

[58] Field of Search .......................... 8/62, 561, 495

[56] References Cited

U.S. PATENT DOCUMENTS 3,697,498  10/1972  Browning et al. ............... 536/4
3,810,882   5/1974  Browning et al. ............... 536/4

FOREIGN PATENT DOCUMENTS 2631318  1/1978  Fed. Rep. of Germany ......... 8/561
2755843  7/1978  Fed. Rep. of Germany ......... 8/495
50-89684  7/1975  Japan ........................ 8/495
2001678  2/1979  United Kingdom .............. 8/561

*Primary Examiner*—Maria Parrish Tungol
*Attorney, Agent, or Firm*—Gabriel Lopez; Hesna J. Pfeiffer

[57] ABSTRACT

A method of printing using polysaccharide gum S-88 as a thickening agent for printing pastes has been developed. The S-88 gum is gellable in the presence of about above 6% to 50% electrolyte. The gelling characteristic of the gum is useful in both single- and multi-phase print systems. The single-phase print system uses a print paste composition containing the S-88 gum together with about 1-6% concentration of electrolyte which, when applied to a substrate, and when the overall moisture content drop (by such methods as heating, etc.) results in a concomitant increase in electrolyte concentration sufficient to cause gelation. The multi-phase print system uses the electrolyte in one phase and the gellable gum in another; i.e., the electrolyte-containing paste or solution with concentration of 6-50% electrolyte is either impregnated on or in the substrate or is present in the printing paste which is applied before or after the S-88 gum-containing paste.

5 Claims, No Drawings

USE OF GUM S-88 IN PRINTING PASTE SYSTEMS

SUMMARY OF THE INVENTION

Polysaccharide S-88, because of its unique interaction with electrolytes, can be used as a printing thickener in a unique system. The substrate can be first impregnated with electrolyte and then printed with the S-88 gum-containing print paste, or printed with a print paste containing S-88 gum and overprinted with electrolyte solution, or printed with a print paste containing both S-88 gum and an electrolyte level just below the gel point of the S-88 and then the total moisture reduced so that the gum gels.

RELATIONSHIP TO THE PRIOR ART

The polysaccharide S-88 is described and claimed in copending U.S. Ser. No. 73,575, filed Sept. 7, 1979, now abandoned. The polysaccharide is prepared by fermentation of a Pseudmonas species ATCC 31554. The bacterial culture can be maintained on Difco nutrient broth or Difco YM broth at 30° C. The gum is isolated from the fermentation broth by precipitation with alcohol such as isopropanol. The gum is a heteropolysaccharide having the following compositions: 10-20% glucouronic acid, 10-30% mannose, 30-40% glucose, 35-45% rhamnose, and 3-7% acetyl groups. In this application, the use of S-88 generally in textile printing and finishing, p. 14, lines 6-7, is maintained. However, the property of S-88 which is its particular and unique interaction with electrolytes was not described in that earlier case.

This invention provides a method for improved fine-line control of printing, on either fabric or paper, or similar process substrates. The gum S-88 can be gelled by concentration of electrolytes from above about 6 to 50%. A softer gel is obtained at between about 4-6% electrolyte. Between about 1.5-4% electrolytes, the gum solutions change in rheological properties.

I have found that, at levels between about 2-5%, electrolytes in an S-88 paste, the paste will be thick enough to print easily, and will not be gelled, but as moisture is lost, such as by heating to dry, the paste will gel, providing sharp line definitions and clarity in printing.

I have also found that this property of S-88 can be exploited in a two-phase printing system. The salt can be either impregnated onto the substrate before printing, or present in a second bath such as for over printing, etc. Since both gum and electrolyte are readily soluble in water, normal washing of fabrics or substrates after printing easily removes any excess material.

Generally, S-88 is used in print pastes by dissolving in amounts of about 0.1-5%. The electrolyte levels, if present in a one-phase print paste system, are about 1 to about 5% (concentrations are based on total amount of final paste). The appropriate dye stuff and additives are also added. The electrolyte which is used can be any electrolyte, including commonly available salts such as NaCl or KCl.

When a two-phase system is used, the S-88 is present in the dye paste at the 0.1-5% levels, and the salt is either impregnated on or in the substrate at levels of between about 5-20%, calculated on the basis of the solution used to contact the substrate; or the salt is present in a separate printing paste, applied either before or after the S-88 containing paste.

More detailed examples illustrating this invention follow.

EXAMPLE 1

Print paste composition:

| | |
|---|---|
| 0.75% | S-88 |
| .5% | dye (disperse) |
| 98.75% | water |

This print paste is made up in the normal manner.
Printing Procedure:
A 100% polyester fabric is padded with a 7.5% NaCl solution to a pick up of 70%. (This puts the salt level at 5.25% on the fabric). This fabric is then printed in the normal way using the print paste containing S-88. The print paste gels after contacting the salt padded fabric, giving a print of exceptional sharpness for the low gum concentration.

EXAMPLE 2

Print paste formula:

| | |
|---|---|
| 1.2% | S-88 |
| 2.0% | KCl |
| 0.6% | acid dye |
| 1.0% | MKP (mono potassium phosphate) |
| 95.20% | water |

The print paste is made up in the normal manner.
Printing Procedure:
A nylon pile upholstery fabric is padded with a 10% KCl solution to a pick up of 100%. (This gives a salt concentration of 10% on the fabric). This fabric is then printed with the print paste containing S-88. The print paste gels when it contacts the salt-containing fabric and the printed image is held in place better than would otherwise be possible.

EXAMPLE 3

Print paste A formula:

| | |
|---|---|
| 0.6% | S-88 |
| 2.0% | MSP (monosodium phosphate) |
| 1.0% | acid dye |
| 0.1% | Terigitol 15-S-9 |
| 96.3% | water |

Print paste B formula:

| | |
|---|---|
| 0.2% | xanthan gum (any non-salt gelling gum) |
| 20.0% | NaCl |
| 0.3% | acid dye |
| 1.0% | acetic acid |
| 0.1% | Tergitol 15-S-9 |
| 78.4% | water |

Printing Procedure:
A nylon carpet is first randomly printed by a TAK unit using Print paste A containing S-88. This is followed by an over print using a Kusters applicator to a pick up of 350% with Print paste B containing 20% salt followed by normal processing. The result is that the TAK print gels, giving control of the print not otherwise obtainable.

An alternate procedure is to apply Print paste B first, followed by TAK application of Print paste A.

FERMENTATION CONDITIONS:

Heteropolysaccharide S-88 is produced during the aerobic fermentation of suitable aqueous nutrient media under controlled conditions via the inoculation with the organism of the unnamed Pseudomonas species. The media are usual media, containing source of carbon, nitrogen and inorganic salts.

In general, carbohydrates (for example, glucose, fructose, maltose, sucrose, xylose, mannitol and the like) can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between about 2% and 4% by weight of the medium. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.5% to 0.2% by weight of the aqueous medium.

Among the nutrient inorganic salts which can be incorporated in the culture media are the customary salts capable of yielding sodium, potassium, ammonium, calcium, phosphate, sulfate, chloride, carbonate, and the like ions. Also included are trace metals such as cobalt, manganese, iron and magnesium.

It should be noted that the media described in the examples are merely illustrative of the wide variety of media which may be employed, and are not intended to be limitative.

One important media characteristic is that when strain S-88 is grown under low $Ca^{++}$ conditions, i.e., in deionized water, or an aqueous system having less than 200 ppm $Ca^{++}$ ions, the resultant gum is readily soluble in solutions without gelling.

The fermentation is carried out at temperatures ranging from about 25° C. to 35° C.; however, for optimum results it is preferable to conduct the fermentation at temperatures of from about 28° C. to 32° C. The pH of the nutrient media for growing the Pseudomonas culture and producing the polysaccharide S-88 can vary from about 6 to 8.

Although the polysaccharide S-88 is produced by both surface and submerged culture, it is preferred to carry out the fermentation in the submerged state.

A small scale fermentation is conveniently carried out by inoculating a suitable nutrient medium with the culture, and after transfer to a production medium permitting the fermentation to proceed at a constant temperature of about 30° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 30° C. for 1-2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are recovered by precipitation with a suitable alcohol such as isopropanol.

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method of producing the S-88 is particularly suited for the preparation of large quantities.

The product is recovered from the fermentation medium by precipitation with a suitable alcohol, such as isopropanol.

EXAMPLE 4

Fermentation Procedure for Producing Heteropolysaccharide S-88

A. Culture Maintenance

The unnamed Pseudomonas organism, ATCC 31554, grows quite well on NA agar at an incubation temperature of 30° C. This organism produces a yellow carotenoid pigment. The colonies on NA are small (only 1-3 mm) by 48 hrs., are convex, and have a gelatinous texture. The typical colony has a tendency to stick tenaciously to the agar surface. Occasionally, a morphological variant may develop which is easy to spot on NA. The variant has a flat colony and does not stick tenaciously to the agar surface. This variant was found to have a decreased activity of S-88 gum production.

B. Seed Preparation

Flask seeds are prepared in YM broth incubated at 30° C.

In this medium the culture will typically give flocculant-type growth followed by viscosity increases with a granular-type appearance. The YM seeds are then used at 24-30 hrs. to inoculate seed medium which is the same as final fermentor medium, except that the phosphate concentration is increased to 0.5%. One-gallon fermentors are used as seed vessels for the 20L and 70L fermentors.

C. Final Fermentor Medium

The following medium gives acceptable results in both 20L and 70L fermentors.

| | |
|---|---|
| Glucose | 3.0% |
| $K_2HPO_4$ | 0.05% |
| AMP | 0.05% |
| $NH_4NO_3$ | 0.09% |
| $MgSO_4 \cdot 7H_2O$ | 0.01% |
| $Fe^{++}$ | 1 ppm |
| HoLe salts | 1 ml/L |

An agitation rate set at 500 rpm in both the 20L and 70L fermentors is desirable. Fermentation times can range from 45-70 hrs. with beer viscosity ranging from 3000 cps to 5000 cps. Conversion efficiencies vary from 31–52% with 3% glucose. Small amounts of commercially available antifoam agent can be used.

Gram stains made from S-88 fermentation beer showed gram-negative cells approximately $1.25\mu \times 2.5\mu$ in size with dark staining polar bodies.

HoLe salts are a trace element solution containing tartrate, magnesium molybdate, $CoCl_3$, $ZnCl_2$, $CuCl_2$, boric acid, manganese chloride and ferrous sulfate.

When a low calcium product is desired, a 30L fermentor medium is as follows:

| 30L Fermentor Medium for Low-Calcium | |
|---|---|
| Deionized water | |
| Glucose | 3.0% |
| $K_2HPO_4$ | 0.05% |
| AMP | 0.05% |
| $MgSO_4 \cdot 7H_2O$ | 0.02% |
| $NH_4NO_3$ | 0.09% |
| Yeast extract | 0.01% |
| HoLe salts | 40 ml |
| Vitamin mix | 25 ml |
| $Fe^{++}$ | 1 ppm |
| $Ca^{++}$ | 2 ppm |

The vitamin mixture is a mixture of 1 $\mu$/ml each of thiamine, cyanocobalamin, patothenate, riboflavin, nicotinic acid, choline, and pyridoxamine; 0.05 $\mu$/ml folic acid and p-aminobenzoic acid; and 0.005 $\mu$/ml biotin.

D. Recovery

Fermentation beer is pasteurized at 167° F. for 10–15 min. Due to the excellent heat stability exhibited by this product, higher pasteurization temperatures with shorter holding times should be acceptable. Good fibers are typically produced under precipitation conditions giving 58–60% spent IPA.

E. Drying

All product recovered thus far has been dried at 50°–55° C. for up to one hour in a forced-air tray dryer.

What is claimed is:

1. A method for printing a textile or substrate comprising contacting the substrate with a printing paste comprising about 0.1–5% heteropolysaccharide S-88; said S-88 being prepared by fermentation under controlled conditions of culture ATCC 31554; and said S-88 containing 10–20% glucuronic acid, and the neutral sugars: mannose, glucose, and rhamnose in the approximate molar ratios of 10–30%; 30–40% and 35–45%, respectively and 3–7% O-acetyl; said substrate either having been pre-wet with a solution comprising 5–20% electrolyte which is an alkali metal halide; or the substrate having been subsequently contacted with a solution comprising 5–20% electrolyte which is an alkali metal halide.

2. The process of claim 1 in which the electrolyte is NaCl or KCl.

3. A printing paste composition comprising an aqueous dye solution having 0.1–5% heteropolysaccharide S-88 as defined in claim 1 and 1–5% salt which is NaCl or KCl.

4. A two-component printing paste system: one component comprising an aqueous dye solution having 0.1%–5% heteropolysaccharide S-88 as defined in claim 1 and, the second component containing 5–20% salt which is an alkali metal halide in aqueous solution, said solution optionally containing dye or similar printing solution.

5. A two-component printing paste system: one component comprising an aqueous dye solution having 0.1%–5% heteropolysaccharide S-88 as defined in claim 1 and, the second component containing 5–20% salt which is NaCl or KCl in aqueous solution, said solution optionally containing dye or similar printing solution.

* * * * *